United States Patent
Menzel

(10) Patent No.: US 9,603,525 B2
(45) Date of Patent: Mar. 28, 2017

(54) SYSTEMS AND METHODS FOR SELECTION OF A PORTABLE TELEMETRY DEVICE

(71) Applicant: Mindray DS USA, Inc., Mahwah, NJ (US)

(72) Inventor: Frank Menzel, Oakland, NJ (US)

(73) Assignee: SHENZHEN MINDRAY BIO-MEDICAL ELECTRONICS CO. LTD., Shenzhen (CN)

( * ) Notice: Subject to any disclaimer, the term of this patent is extended or adjusted under 35 U.S.C. 154(b) by 259 days.

(21) Appl. No.: 14/461,096

(22) Filed: Aug. 15, 2014

(65) Prior Publication Data
US 2016/0045111 A1 Feb. 18, 2016

(51) Int. Cl.
*A61B 5/00* (2006.01)

(52) U.S. Cl.
CPC .............. *A61B 5/002* (2013.01); *A61B 5/742* (2013.01); *A61B 2560/0214* (2013.01); *A61B 2560/0456* (2013.01); *A61B 2560/0487* (2013.01)

(58) Field of Classification Search
CPC .... A61B 2560/0214; A61B 2560/0456; A61B 2560/0487; A61B 5/002; A61B 5/742
See application file for complete search history.

(56) References Cited

U.S. PATENT DOCUMENTS

| | | | | |
|---|---|---|---|---|
| 7,847,515 B2 * | 12/2010 | Schroeck | ............ | H01M 2/1022 320/106 |
| 2008/0079391 A1 * | 4/2008 | Schroeck | ............ | H01M 2/1022 320/106 |
| 2009/0112099 A1 * | 4/2009 | Kurokawa | ............... | A61B 8/00 600/459 |

* cited by examiner

*Primary Examiner* — Sisay Yacob
(74) *Attorney, Agent, or Firm* — Kory D. Christensen; Stoel Rives LLP

(57) ABSTRACT

A system comprising for selecting a portable telemetry device includes a status component, a request component, a selection component and an indication component. The status component is configured to determine a device status for a plurality of portable telemetry devices docked in a charging station. The request component is configured to receive a request to use at least one of the plurality of portable telemetry devices. The selection component is configured to select, in response to the request, a portable telemetry device based on device statuses for the plurality of portable telemetry devices. The indication component is configured to indicate selection of the portable telemetry device to a user.

12 Claims, 4 Drawing Sheets

SYSTEMS AND METHODS FOR SELECTION OF A PORTABLE TELEMETRY DEVICE

TECHNICAL FIELD

The present disclosure relates to medical monitoring and more particularly relates to systems, methods, and devices for selecting a portable telemetry device.

DETAILED DESCRIPTION OF PREFERRED EMBODIMENTS

Figure 1:
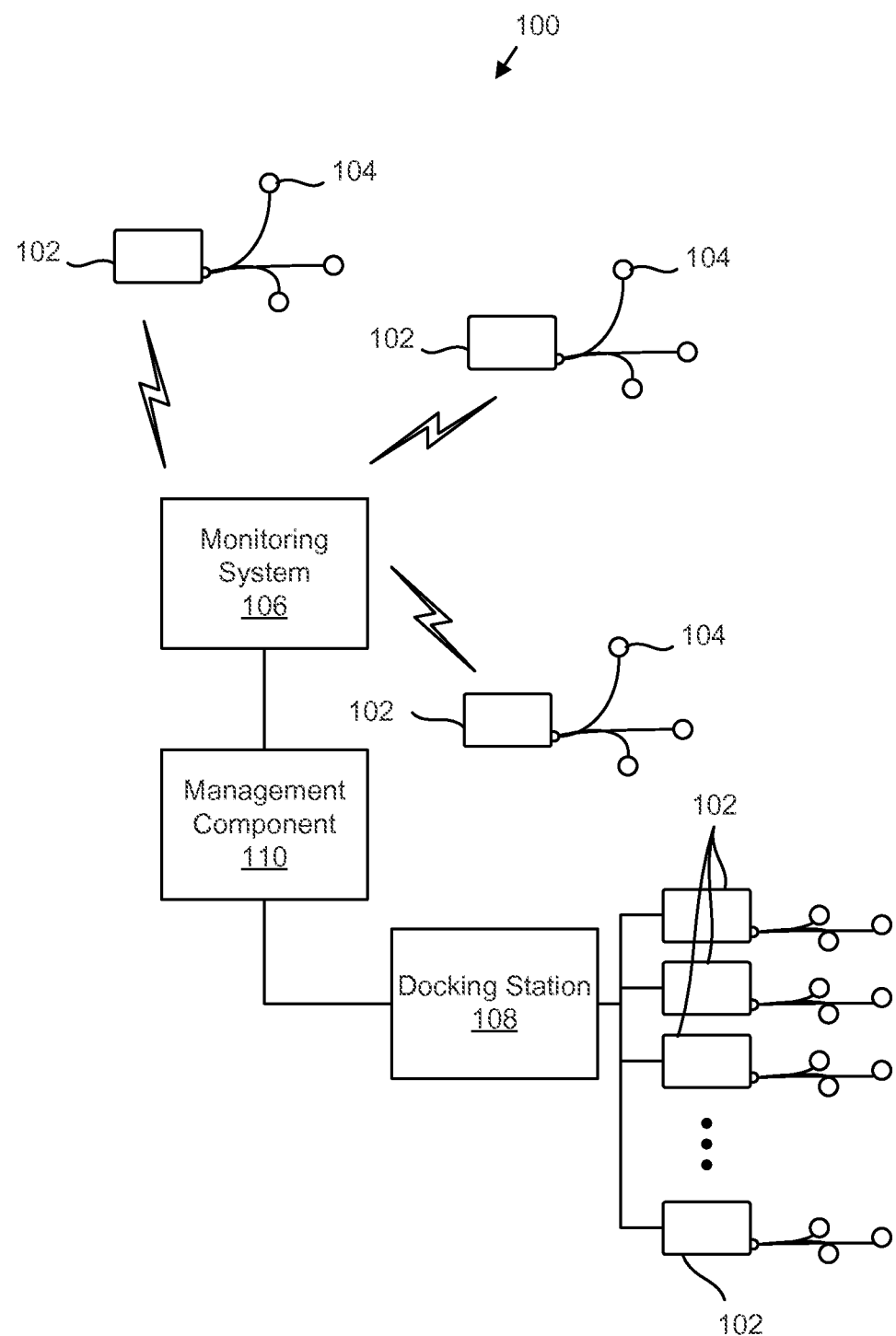
FIG. 1 is a schematic block diagram illustrating a telemetry system, according to one embodiment.

Modern technology practice makes extensive use of electronic monitoring of vital signs and other physiological parameters of patients. In some cases, remote monitoring of physiological parameters, or telemetry, is used to allow nurses, doctors, and/or computing devices to determine the health of a patient or detect problems with the patient when the nurse or doctor is not with the patient. In some cases, wireless telemetry devices worn by a patient may allow the patient to move around and/or be easily moved between locations while maintaining monitoring of the patient's vital signs. One example of a portable telemetry device is the Mindray Telepack®.

In a hospital or medical facility, multiple portable telemetry devices may be used to monitor multiple patients. For example, a portable telemetry device may be available for each room or each bed of a hospital or unit of a hospital. When portable telemetry devices are not in use, they may be docked to recharge or otherwise maintain them. For example, the portable telemetry device software may be updated, a storage area may be re-imaged, stored data may be deleted or modified, a status of the device may be determined, or the like.

When a patient needs to be set up with a portable telemetry device, it may be desirable for a nurse or medical staff to pick a portable telemetry device based on a relative status compared to other available portable telemetry devices. For example, it may be desirable to select a portable telemetry device that is completely recharged, or has the greatest amount of charged stored in its battery. Similarly, it may be desirable to select a portable telemetry device that has updated software, has finished a management procedure, has a lowest number of usage hours, has a lowest number of battery recharge cycles, or the like. By selecting based on a device status, it may increase the likelihood that a selected device will work properly and have sufficient charge to run for a desired length of time, thus increasing usage life of the devices. However, Applicants have recognized that it can be difficult or time consuming for a nurse or staff member to determine this information and select a device.

Based on the foregoing, Applicants have developed systems, methods, and devices for automating selection of a portable telemetry device. In one embodiment, a system for selecting a portable telemetry device includes a status component, a request component, a selection component, and an indication component. The status component determines a device status for a plurality of portable telemetry devices docked in a charging station. The request component receives a request to use at least one of the plurality of portable telemetry devices. The selection component selects, in response to the request, a portable telemetry device from the plurality of portable telemetry devices docked at a charging station. The selection component also selects the portable telemetry device based on device statuses for the plurality of portable telemetry devices. The indication component indicates selection of the portable telemetry device by a user.

When not in use, one or more portable telemetry devices may be connected to a docking station, such as a charging station located at a central nurses' station or monitoring area. In one embodiment, the docking station is a smart device which may be connected to a central monitoring system, either directly or via a network. The docking station, or central monitoring system, can program the portable telemetry devices and read their device statuses. When a clinician wishes to use a portable telemetry device, the clinician may select a location displayed on the central monitor for which a portable telemetry device is needed. The smart docking station or central monitoring system may then pick a portable telemetry device based on one or more of battery charge level, battery lifecycle, software version, hours of usage, or the like. After selection, the docking station or central monitoring system programs the selected portable telemetry device to communicate/operate in the selected location. In one embodiment, the selected portable telemetry device may also be associated with or programmed to correspond to a specific patient, room, or bed. When the selected portable telemetry device is ready to go, a visual indication, such as an LED or display of the selected portable telemetry device, may be lit (or have an altered state) to indicate to the clinician which portable telemetry device can be used and that it is ready. Alternatively or in addition, audio indications may be used. The clinician can take the corresponding selected portable telemetry device and use it for patient monitoring. Thus, a clinician can easily obtain a portable telemetry device that is ready for usage.

A detailed description of systems and methods consistent with embodiments of the present disclosure is provided below. While several embodiments are described, it should be understood that this disclosure is not limited to any one embodiment, but instead encompasses numerous alternatives, modifications, and equivalents. In addition, while numerous specific details are set forth in the following description in order to provide a thorough understanding of the embodiments disclosed herein, some embodiments can be practiced without some or all of these details. Moreover, for the purpose of clarity, certain technical material that is known in the related art has not been described in detail in order to avoid unnecessarily obscuring the disclosure.

Turning to the figures, FIG. 1 is a schematic diagram illustrating one embodiment of a telemetry system 100. The telemetry system 100 includes a plurality of portable telemetry devices 102, a monitoring system 106, a docking station 108, and a management component 110. The portable telemetry devices 102 are attached to sensors 104 which may be used to gather patient data from an attached or corresponding patient. Although the management component 110 is illustrated as logically separate from the monitoring system 106 and the docking station 108, in some embodiments, the management component 110 may be incorporated into one or both of the monitoring system 106 and the docking station 108. The monitoring system 106, docking station 108, management component 110, and portable telemetry devices 104 may be in communication via direct or network wireless or wired connections.

In one embodiment, the portable telemetry device 102 includes a telemetry device worn by a patient. For example, the patient may be free to walk or move while wearing the portable telemetry device 102 due to size and/or a capability for wireless communication. The portable telemetry device 102 may include a portable device comprising a housing containing a processor, circuitry, computer readable memory, antenna, radios, a battery, and/or the like. The portable telemetry device 102 may be small enough to be worn by a patient and allow the patient to move freely. The telemetry device 102 may include one or more ports for coupling to sensors 104 and receiving signals from the sensors. The portable telemetry device 102 may include a human-machine interface, which may include a display, one or more buttons, and/or indicator lights to allow a human to determine a status of the portable telemetry device 102, enter information, or otherwise interact with the portable telemetry device 102.

In one embodiment, the portable telemetry device 102 is in wireless communication with the monitoring system 106. Connected to the telemetry device 102 are a plurality of sensors 104 which may be used to measure patient parameters and/or obtain patient waveforms. For example, the sensors 104 may include one or more electrocardiography (ECG) sensors, a pulse oximetry sensor (e.g., SpO2), and/or other sensors. The portable telemetry device 102 may receive signals from the sensors 104 as analog or digital data signals indicating a physiological condition of a patient. The portable telemetry device 102 may transmit physiological data to the monitoring system 106 for monitoring, storage, or the like. For example, the telemetry device 102 may forward processed or unprocessed sensor data to the monitoring system 106 so that a doctor, nurse, or other medical personnel can monitor a condition of the patient.

The monitoring system 106 may include a computing device such as a computer, server, or the like. The monitoring system 106 may include a processor, circuitry, computer readable memory, antenna, radios, communication ports, and/or the like. In one embodiment, the monitoring system 106 includes a computing system for a central nursing station. The monitoring system 106 may include a computing system for an intensive care ward, step-down ward, or in-patient ward.

The monitoring system 106 receives the physiological data from the portable telemetry device 102 and stores and/or processes the physiological data. In one embodiment, the monitoring system 106 stores the physiological data in memory for later access and/or analysis. In one embodiment, the monitoring system 106 processes the physiological data to detect problems for the patient, detect whether there is an alarm condition, or perform other analysis. For example, the monitoring system 106 may report an alarm condition to a nurse, doctor, or other medical personnel. The monitoring system 106 may also provide control data to the portable telemetry device 102 to configure alarm settings, reset alarms, determine a state or location of the portable telemetry device 102, transfer stored data, or otherwise configure operation of the portable telemetry device 102. In one embodiment, the telemetry system 100 may send and receive control data between the portable telemetry device 102 and the monitoring system 106 to determine that messages were received or that instructions corresponding to control data were performed.

In one embodiment, the docking station 108 includes a physical port or a device where portable telemetry device 102 can be connected or placed when not in use. For example, the docking station 108 may include a plurality of slots, ports, or connections where the portable telemetry device 102 can be docked for storage, recharging, or performance of management tasks. In one embodiment, a physical connection may not be needed as wireless charging and communication can be provided to the portable telemetry devices 102. In one embodiment, the docking station 108 includes a physical location where portable telemetry devices 102 may be kept when not in use. In one embodiment, the docking station 108 may include processing circuitry or other circuitry to provide smart features to the docking station. For example, the management component 110 may be integrated into the docking station 108, or the docking station may be configured to communicate with the management component 110 or monitoring system 106 to implement charging or other management procedures in relation to the portable telemetry devices 102.

The management component 110 is configured to manage the portable telemetry devices 102. For example, the management component 110 may manage portable telemetry devices 102 which are docked in or at the docking station 108. In one embodiment, the management component 110 manages the portable telemetry devices 102 by determining a device status for each portable telemetry device 102 docked in the docking station 108. For example, the portable telemetry devices 102 may send messages to the management component 110 via the docking station 108 indicating one or more of a battery charge level, a software version, a total usage time for the device, a number of total battery lifecycles performed or remaining, or the like. The management component 110 may store the device status information.

In one embodiment, the management component 110 receives a request to use a portable telemetry device 102 from a user. For example, a user may provide a request to use a portable telemetry device 102 to the monitoring system 106. The monitoring system 106 may forward information regarding the request to the management component 110. The management component 110 may automatically select an available portable telemetry device 102 based on corresponding device statuses. The management component 110 may also provide an indication of which portable telemetry device 102 was selected. For example, the management component 110 may send a signal to a selected portable telemetry device 102 to light up a display or indicator light so that a user can see which portable telemetry device 102 was selected for usage.

Figure 2:
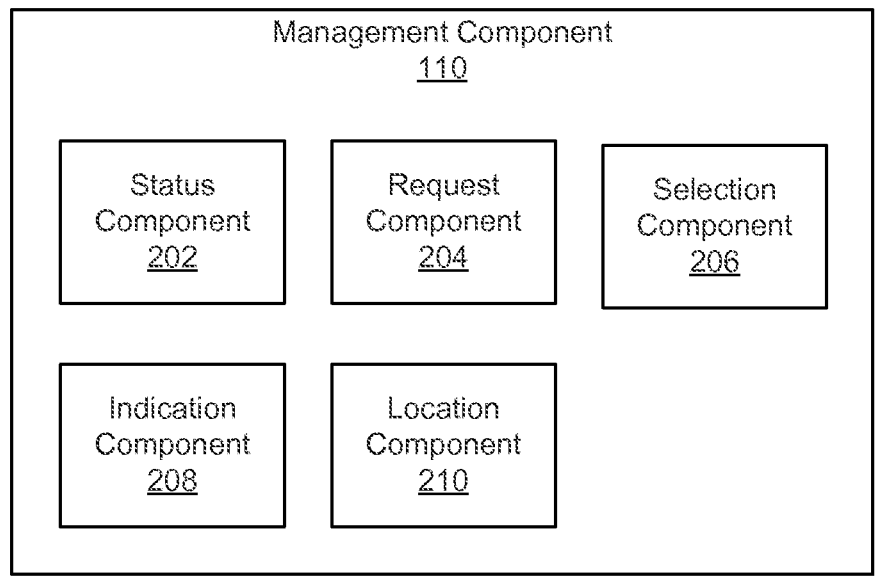
FIG. 2 is a schematic block diagram illustrating a management component, according to one embodiment.

FIG. 2 is a schematic block diagram of the management component 110. The management component 110 includes a status component 202, a request component 204, a selection component 206, and an indication component 208. The components 202-208 are given by way of example only and may not all be included in all embodiments.

The status component 202 is configured to determine a device status of one or more portable telemetry devices 102. In one embodiment, the status component 202 determines device statuses for each portable telemetry device 102 connected to a docking station 108. For example, the portable telemetry devices 102 attached to the docking station 108 may be connected via a connector that charges each portable telemetry device 102 and also provides communication with the management component 110 or monitoring system 106. In one embodiment, the status component 202 may query each portable telemetry device 102 as to its current device status. In one embodiment, the portable telemetry devices 102 may each provide a current status. The status component 202 may store the device statuses for the portable telemetry devices 102 in memory, for access when needed. In one embodiment, the status component 202 may only determine the device statuses for each of the portable telemetry devices 102 when a request to select a portable telemetry device 102 is received. Example device status information that may be determined include a battery charge level, a battery lifecycle, a software version, hours of usage for the portable telemetry device 102, whether a management task has been completed on the portable telemetry device 102, or the like.

The request component 204 may receive a request to use an available portable telemetry device 102. For example, medical staff may wish to use a portable telemetry device 102 with a patient and may wish to select and assign a portable telemetry device 102 to that patient so that they may monitor medical parameters of the patient. In one embodiment, the request component 204 may receive a request from a monitoring system 106 in response to a user indicating a location or patient for desired usage of a portable telemetry device 102. The request may indicate a location for usage, a patient identifier, and/or an indication that a portable telemetry device 102 will need to be selected and used with the patient in the indicated location. The request component 204 may receive the request and notify a selection component 206 to select a portable telemetry device 102 for the specific patient and/or location.

The selection component 206 is configured to select a portable telemetry device 102. In one embodiment, the selection component 206 selects the portable telemetry device 102 in response to the request component 204 receiving a request. In one embodiment, the selection component 206 selects a portable telemetry device 102 from a plurality of portable telemetry devices 102 docked at a docking station 108 or which are otherwise not currently in use.

In one embodiment, the selection component 206 selects one of the portable telemetry devices 102 based on the device statuses of the available portable telemetry devices 102. Example device statuses may include a battery charge level, a battery lifecycle, a software version, hours of usage for the portable telemetry device 102, whether a management task has been completed on the portable telemetry device 102, or the like. The battery charge level may indicate a percent charge of the battery, an amount of time left on the battery to use the portable telemetry device 102, or an amount of power currently stored within the device. For example, the selection component 206 may select a portable telemetry device 102 that is fully charged or has a highest battery charge level. The battery lifecycle information may include how many charge/discharge cycles the battery of the portable telemetry device 102 has been through. For example, it may be desirable to select a portable telemetry device 102 that has had the fewest charge/discharge cycles to allow a collection of portable telemetry devices 102 to wear evenly over time.

The software version may indicate a version of software operating the portable telemetry device 102. For example, a user may want to select a portable telemetry device 102 with the most up-to-date software. The hours of usage may indicate the total number of usage hours for the portable telemetry device 102. For example, a user may want to select a portable telemetry device 102 that has the fewest total usage hours to allow the portable telemetry devices 102 to wear evenly over time. In a similar manner, the selection component 206 may select a portable telemetry device 102 based on a hardware version or other hardware information of a portable telemetry device 102. The status of a management task may indicate whether device management has been performed on a portable telemetry device 102 since its last usage. Management tasks may include updating software, resetting memory, removing patient data, restarting the device, or the like. For example, users may want to select only portable telemetry devices 102 that have had all the needed management tasks performed.

In one embodiment, the selection component 206 selects a portable telemetry device 102 based on multiple types of device statuses. For example, different types of device statuses may be weighted or prioritized differently. In one embodiment, the battery charge level will be checked first and then a software version can be checked second on those that have a sufficiently high battery charge level. As another example, the selection component 206 may determine whether a minimum level for each device status type is met. For example, the battery may need to be at least 80% recharged and the software must be at least a specific version.

The indication component 208 provides an indication to a user of the selected portable telemetry device 102 as selected by the selection component 206. For example, after the selection component 206 selects a specific portable telemetry device 102, the indication component 208 may indicate on a display or interface that the specific portable telemetry device 102 has been selected. In one embodiment, the indication component 208 sends a selection message to the selected portable telemetry device 102 to cause the selected portable telemetry device 102 to indicate, via a user interface, that the device has been selected. For example, the portable telemetry device 102 may light an indicator light, light a display, make a sound, vibrate, and/or provide other feedback to indicate to the user which portable telemetry device 102 has been selected. In one embodiment, an indication of the selected portable telemetry device 102 may be displayed on a display, such as a display of the monitoring system 106.

The location component 210 is configured to receive information regarding a usage location or patient for which a portable telemetry device 102 will be used. For example, the request received by the request component 204 may include a location and/or patient information indicating which room, bed, patient, and/or region of a hospital a requested device will be used. In one embodiment, the location component 210 may assign a portable telemetry device 102 selected by the selection component 206 to the corresponding location or patient. For example, the location component 210 may send patient or location information to the selected portable telemetry device 102 which can store that information to track its assigned location. As another example, the location component 210 may assign the selected portable telemetry device 102 by updating a location assignment with the monitoring system 106 or a database tracking assigned locations.

Figure 3:
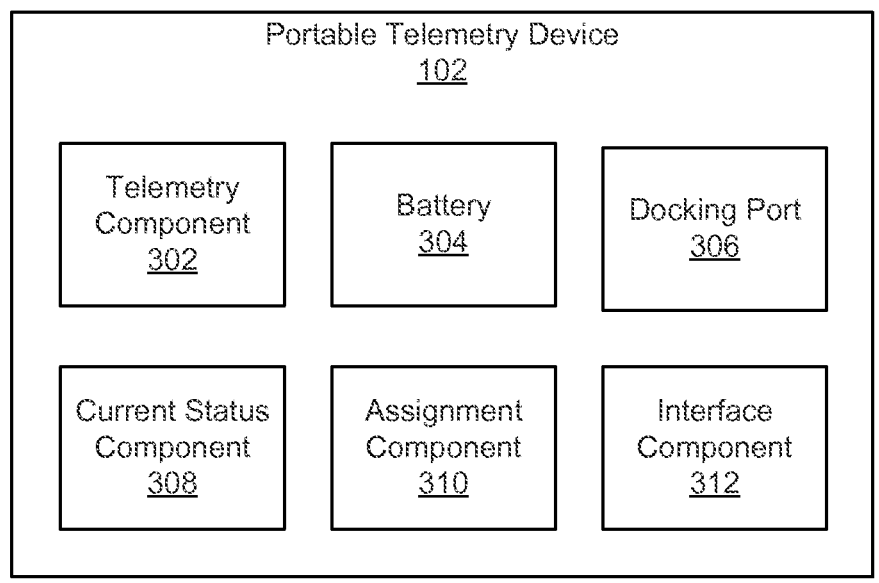
FIG. 3 is a schematic block diagram illustrating a portable telemetry device, according to one embodiment.

FIG. 3 is a schematic block diagram of a portable telemetry device 102. The portable telemetry device 102 includes a telemetry component 302, battery 304, docking port 306, current status component 308, assignment component 310, and interface component 312. The components 302-312 are given by way of example only and may not all be included in all embodiments.

The telemetry component 302 is configured to gather patient data from one or more sensors 104 and provide the patient data, or information about the patient data, to the monitoring system 106. In one embodiment, the telemetry component 302 includes one or more sensor ports for receiving the patient data. In one embodiment, the telemetry component 302 includes an antenna or communication port to communicate the patient data to the monitoring system 106. For example, the telemetry component 302 may wirelessly communicate the patient data to the monitoring system 106 such that the portable telemetry device 102 may provide patient monitoring even when the patient needs to leave a room or bed.

The battery 304 may store electrical energy for usage by the portable telemetry device 102. For example, the battery 304 may act as a power supply to allow the portable telemetry device 102 to gather and/or report data even when the portable telemetry device 102 is not plugged into an outlet or external power source.

The docking port 306 may include a charging and/or communication port to allow the telemetry device 102 to be recharged and/or communicate with a docking station 108. The docking port 306 may include a physical connection to provide charging and/or communication through a wired connection or may include proximity charging or communication such that the portable telemetry device 102 may be charged wirelessly and/or communicate wirelessly with the management component 110. In one embodiment, the battery 304 may be recharged by electrical power provided via the docking port 306. In one embodiment, the device status information, software updates, and/or other information may be communicated via the docking port 306.

The current status component 308 is configured to determine a current status of the portable telemetry device 102 and send the current status to the management component 110. In one embodiment, the current status component 308 may determine and/or send a device status comprising any of the device statuses discussed herein. For example, the current status component 308 may send a current status comprising a battery charge level, software version, hardware version, or the like via the docking port 306 to the management component 110. In one embodiment, the current status component 308 determines and/or sends the current device status information in response to a request from the management component 110. In one embodiment, the current status component 308 may only determine/send the device status when the portable telemetry device 102 is connected to the docking station 108, such as via the docking port 306.

The assignment component 310 is configured to receive a selection indication from the management component 110. For example, when the portable telemetry device 102 is selected, the assignment component 310 may receive a selection indication indicating that the portable telemetry device 102 has been selected. In one embodiment, the assignment component 310 may store an indication that the portable telemetry device 102 has been selected and/or may store an indication of a location or patient to which the portable telemetry device 102 is assigned.

The interface component 312 provides a human-machine interface to receive input from a user and/or to indicate a status or other information to a user. In one embodiment, the interface component 312 includes a display which can be used to provide a graphical user interface to convey visual information such as text, images, or the like. In one embodiment, the interface component 312 includes an indicator light with two or more states to indicate a state of the portable telemetry device 102 to the user. Example states may include an on state, an off state, a blinking state, or different color states. In one embodiment, the interface component 312 may include one or more buttons, a touch screen, or other device for user input.

In one embodiment, the interface component 312 is configured to indicate to a user that the portable telemetry device 102 has been selected. For example, the interface component 312 may change a state of a display, indicator light, or the like after the assignment component 310 receives an assignment indication. For example, the state of a display, indicator light, or other portion of the interface component 312 may be different from other portable telemetry devices 102 docked at a docking station 108. A user may be able to see the new state, take the portable telemetry device 102, and begin using the portable telemetry device 102 with very little effort to determine which portable telemetry device 102 to select and/or which portable telemetry device 102 has been selected.

Figure 4:
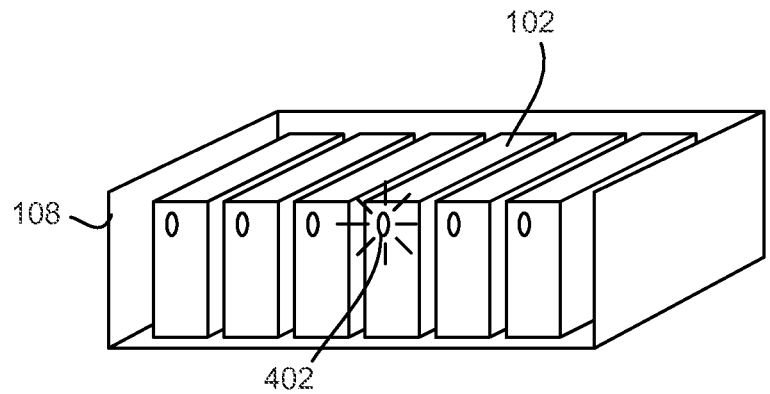
FIG. 4 is a perspective view of portable telemetry devices at a docking station, according to one embodiment.

FIG. 4 is a perspective view of one or more portable telemetry devices 102 docked in a docking station 108. Each of the portable telemetry devices 102 includes an indicator light 402. In FIG. 4, a user can determine which portable telemetry device 102 was selected because only one of the indicator lights 402 is lit. A user may be able to see a different state of the lit indicator light 402, take the portable telemetry device 102, and begin using the portable telemetry device 102 with very little effort to determine which portable telemetry device 102 to select and/or which portable telemetry device 102 has been selected.

Figure 5:
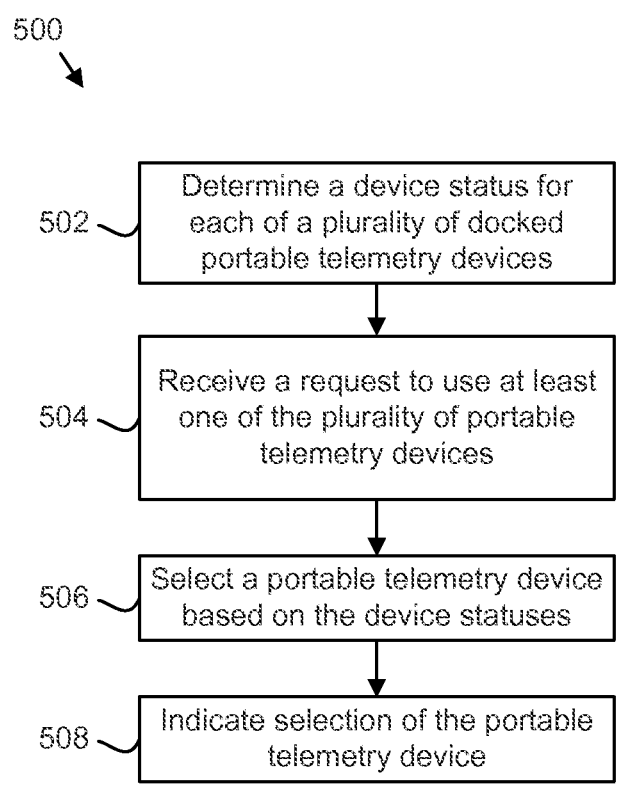
FIG. 5 is a schematic flow chart diagram illustrating a method for selecting a portable telemetry device, according to one embodiment.

FIG. 5 is a schematic flow chart diagram illustrating a method 500 for selecting a portable telemetry device 102, according to one embodiment. The method 500 may be performed by a management component 110, such as the management component 110 of FIG. 2.

The method 500 begins and a status component 202 determines 502 a device status for a plurality of portable telemetry devices 102 docked in a charging station. For example, the status component 202 may determine 502 a device status for each portable telemetry device 102 which is not currently assigned to a patient. The status component 202 may determine 502 the device status by requesting and/or receiving status information from the portable telemetry devices 102.

A request component 204 receives 504 a request to use at least one of the plurality of portable telemetry devices 102. For example, a user may provide input to the management component 110 or a monitoring system 106 indicating a request to use a portable telemetry device 102. A selection component 206 selects 506, in response to the request, a portable telemetry device 102 from the plurality of available portable telemetry devices 102. For example, the available portable telemetry devices 102 may include portable telemetry devices 102 docked at a charging station. In one embodiment, the selection component 206 selects 506 the portable telemetry device 102 based on device statuses determined 502 by the status component 202.

An indication component 208 indicates 508 selection of the portable telemetry device 102 to a user. For example, the indication component 208 may indicate 508 the selection by changing a state of an indicator light, display, speaker, or any other output or interface component of a portable telemetry device 102 or telemetry system 100.

Figure 6:
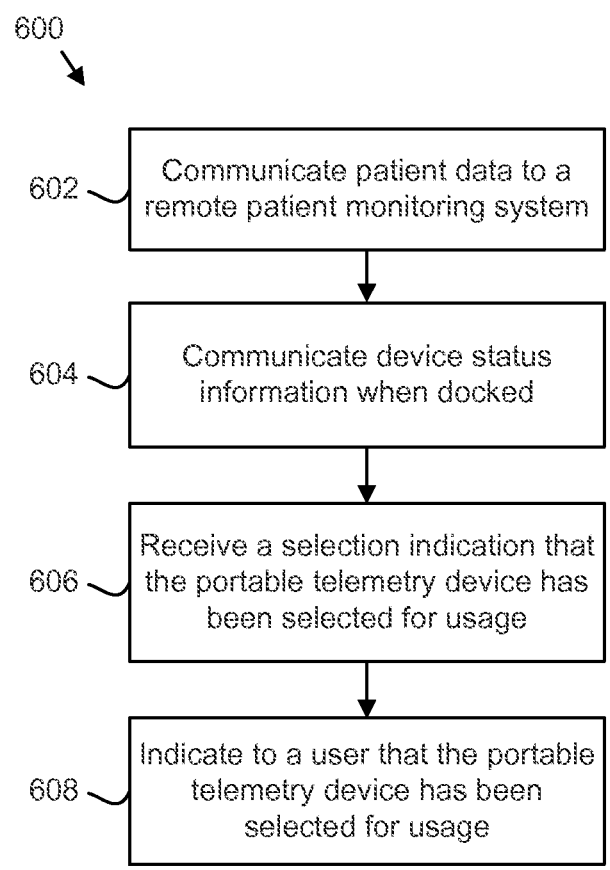
FIG. 6 is a schematic flow chart diagram illustrating another method for selecting a portable telemetry device, according to one embodiment.

FIG. 6 is a schematic flow chart diagram illustrating a method 600 for selecting a portable telemetry device 102, according to one embodiment. The method 600 may be performed by a portable telemetry device 102, such as the portable telemetry device 102 of FIG. 3.

The method 600 begins and a telemetry component 302 communicates 602 patient data to a remote patient monitoring system. A current status component 308 communicates 604 device status information for the portable telemetry device 102 when the portable telemetry device 102 is docked. For example, a docking port 306 may be in wired or wireless communication with a docking station 108 or recharging station.

An assignment component 310 receives 606 a selection indication that the portable telemetry device 102 has been selected for usage. An interface component 312 indicates 608 to a user that the portable telemetry device 102 has been selected for usage. For example, the interface component 312 may indicate 608 that the portable telemetry device 102 has been selected by changing a state of an indicator light or display of the portable telemetry device 102.

Various techniques, or certain aspects or portions thereof, may take the form of program code (i.e., instructions) embodied in tangible media, such as floppy diskettes, CD-ROMs, hard drives, a non-transitory computer readable storage medium, or any other machine-readable storage medium, wherein when the program code is loaded into and executed by a machine, such as a computer, the machine becomes an apparatus for practicing the various techniques. In the case of program code execution on programmable computers, the computing device may include a processor, a storage medium readable by the processor (including volatile and non-volatile memory and/or storage elements), at least one input device, and at least one output device. The volatile and non-volatile memory and/or storage elements may be a RAM, an EPROM, a flash drive, an optical drive, a magnetic hard drive, or another medium for storing electronic data. The eNB (or other base station) and UE (or other mobile station) may also include a transceiver component, a counter component, a processing component, and/or a clock component or timer component. One or more programs that may implement or utilize the various techniques described herein may use an application programming interface (API), reusable controls, and the like. Such programs may be implemented in a high-level procedural or an object-oriented programming language to communicate with a computer system. However, the program(s) may be implemented in assembly or machine language, if desired. In any case, the language may be a compiled or interpreted language, and combined with hardware implementations.

It should be understood that many of the functional units described in this specification may be implemented as one or more components, which is a term used to more particularly emphasize their implementation independence. For example, a component may be implemented as a hardware circuit comprising custom very large scale integration (VLSI) circuits or gate arrays, off-the-shelf semiconductors such as logic chips, transistors, or other discrete components. A component may also be implemented in programmable hardware devices such as field programmable gate arrays, programmable array logic, programmable logic devices, or the like.

Components may also be implemented in software for execution by various types of processors. An identified component of executable code may, for instance, comprise one or more physical or logical blocks of computer instructions, which may, for instance, be organized as an object, a procedure, or a function. Nevertheless, the executables of an identified component need not be physically located together, but may comprise disparate instructions stored in different locations that, when joined logically together, comprise the component and achieve the stated purpose for the component.

Indeed, a component of executable code may be a single instruction, or many instructions, and may even be distributed over several different code segments, among different programs, and across several memory devices. Similarly, operational data may be identified and illustrated herein within components, and may be embodied in any suitable form and organized within any suitable type of data structure. The operational data may be collected as a single data set, or may be distributed over different locations including over different storage devices, and may exist, at least partially, merely as electronic signals on a system or network. The components may be passive or active, including agents operable to perform desired functions.

Reference throughout this specification to "an example" means that a particular feature, structure, or characteristic described in connection with the example is included in at least one embodiment of the present invention. Thus, appearances of the phrase "for example" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on its presentation in a common group without indications to the contrary. In addition, various embodiments and examples of the present invention may be referred to herein along with alternatives for the various components thereof. It is understood that such embodiments, examples, and alternatives are not to be construed as de facto equivalents of one another, but are to be considered as separate and autonomous representations of the present invention.

It will be obvious to those having skill in the art that many changes may be made to the details of the above-described embodiments without departing from the underlying principles of the invention. The scope of the present invention should, therefore, be determined only by the following claims.

The invention claimed is:

1. A portable telemetry device selection system comprising:
   a status component in electronic communication with each of a plurality of portable telemetry devices, the status component configured to electronically determine at least two device statuses for each of the plurality of portable telemetry devices docked in a charging station;
   a request component configured to receive an electronic request from a user via an electronic user selection device to use at least one of the plurality of portable telemetry devices;
   a selection component configured to select, in response to the electronic request, a portable telemetry device from the plurality of portable telemetry devices docked at the charging station based on the at least two device statuses for the plurality of portable telemetry devices, the at least two device statuses including at least two of:

a battery charge level of the at least one of the plurality of portable telemetry devices, a battery lifecycle of the at least one of the plurality of portable telemetry devices, a software version of the at least one of the plurality of portable telemetry devices, and a total usage time of the at least one of the plurality of portable telemetry device; and an indication component configured to indicate to the user which of the plurality of portable telemetry devices has been selected for the user.

2. The system of claim 1, further comprising a location component configured to receive an indication of a usage location for the at least one of the plurality of portable telemetry devices.

3. The system of claim 2, further comprising an assignment component configured to assign the at least one of the portable telemetry devices to the usage location.

4. The system of claim 1, wherein the indication component is configured to indicate selection by changing a state of an indicator light on the selected portable telemetry device.

5. The system of claim 1, wherein the indication component is configured to indicate selection by changing a state of a display on the selected portable telemetry device.

6. A method for improved selection of a portable telemetry device comprising:

determining a device status, via an electronically connected status component, for a plurality of portable telemetry devices docked in a charging station;

receiving an electronic request from a user via an electronic user selection device to use at least one of the plurality of portable telemetry devices;

selecting a portable telemetry device from the plurality of portable telemetry devices docked at a charging station, wherein the selection component is configured to select the portable telemetry device based on at least two device statuses for the plurality of portable telemetry devices, the at least two device statuses including at least two of:

a battery charge level of the at least one of the plurality of portable telemetry devices, a battery lifecycle of the at least one of the plurality of portable telemetry devices, a software version of the at least one of the plurality of portable telemetry devices, and a total usage time of the at least one of the plurality of portable telemetry device; and indicating, via an indication component, a selection of one of the portable telemetry devices to the user.

7. The method of claim 6, further comprising receiving an indication of a usage location for the at least one of the plurality of portable telemetry devices.

8. The method of claim 7, further comprising assigning the at least one of the portable telemetry devices to the usage location.

9. The method of claim 6, wherein indicating the selection comprises changing a state of an indicator light on the selected portable telemetry device.

10. The method of claim 6, wherein indicating the selection comprises changing a state of a display on the selected portable telemetry device.

11. A portable telemetry device comprising:

a battery;

a docking port configured to connect to a recharging station to recharge the battery;

a telemetry component configured to electronically communicate patient data to a remote patient monitoring system;

a current status component configured to electronically communicate device status information for the portable telemetry device when the docking port is communicatively connected to the recharging station, wherein the communicated device status information comprises at least two of:

a battery charge level of the portable telemetry device, a battery lifecycle of the portable telemetry device, a software version of the portable telemetry device, and a total usage time of the portable telemetry device;

an assignment component configured to receive a selection indication that the portable telemetry device has been selected for usage; and an interface component configured to, in response to the selection indication, indicate to a user that the portable telemetry device has been selected for usage.

12. The portable telemetry device of claim 11, wherein the interface component comprises one or more of an indicator light and a display screen and wherein the interface component is configured to indicate that the portable telemetry device has been selected by changing a state of one or more of the indicator light and the display screen.

* * * * *